US00PP16133P2

(12) United States Plant Patent
Hooijman

(10) Patent No.: US PP16,133 P2
(45) Date of Patent: Nov. 29, 2005

(54) ***ASTER* PLANT NAMED 'ESMGUYANA'**

(50) Latin Name: *Aster hybrida*
Varietal Denomination: Esmguyana

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 38 days.

(21) Appl. No.: 10/968,802

(22) Filed: Oct. 19, 2004

(51) Int. Cl.[7] ..... A01H 5/00
(52) U.S. Cl. ..... Plt./355
(58) Field of Search ..... Plt./355

*Primary Examiner*—Kent Bell
(74) *Attorney, Agent, or Firm*—C. A. Whealy

(57) ABSTRACT

A new and distinct cultivar of cut flower *Aster* plant named 'Esmguyana', characterized by its strong and erect flowering stems; symmetrical branching habit with long lateral branches; dark green-colored foliage; early, uniform and freely flowering habit; daisy-type inflorescences with dark purple violet-colored ray florets; flat and straight ray florets; and excellent postproduction longevity.

1 Drawing Sheet

Botanical classification/cultivar designation: *Aster hybrida* cultivar Esmguyana.

BACKGROUND OF THE INVENTION

The present Invention relates to a new and distinct cultivar of cut flower *Aster* plant, botanically known as *Aster hybrida* and hereinafter referred to by the name 'Esmguyana'.

The new *Aster* is a product of a planned breeding program conducted by the Inventor in El Quinche, Pichincha, Ecuador. The objective of the breeding program is to create new cut flower *Aster* cultivars with durable leaves, strong and long stems, desirable floret colors and good postproduction longevity.

The new *Aster* originated from a cross-pollination made by the Inventor in El Quinche, Pichincha, Ecuador in February, 2000, of a proprietary *Aster* selection identified as Line 11, not patented, as the female, or seed, parent with an unknown *Aster* selection, not patented, as the male, or pollen, parent. The new *Aster* was discovered and selected by the Inventor as a single flowering plant within the progeny of the stated cross-pollination grown in a controlled environment in El Quinche, Pichincha, Ecuador. The selection of this plant was based on its durable foliage, strong and long stems and desirable inflorescence form and attractive ray floret color.

Asexual reproduction of the new *Aster* by vegetative tip cuttings was first conducted in El Quinche, Pichincha, Ecuador in January, 2001. Asexual reproduction by cuttings has shown that the unique features of this new *Aster* are stable and reproduced true to type in successive generations.

SUMMARY OF THE INVENTION

The cultivar Esmguyana has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Esmguyana'. These characteristics in combination distinguish 'Esmguyana' as a new and distinct cut flower *Aster:*

1. Strong and erect flowering stems.
2. Symmetrical branching habit with long lateral branches.
3. Dark green-colored foliage.
4. Early, uniform and freely flowering habit.
5. Daisy-type inflorescences with dark purple violet-colored ray florets.
6. Flat and straight ray florets.
7. Excellent postproduction longevity.

Plants of the new *Aster* can be compared to plants of the female parent selection. Plants of the new *Aster* differ primarily from plants of the female parent selection in ray floret coloration as plants of the female parent selection have pink-colored ray florets.

Plants of the new *Aster* can be compared to plants of the cultivar Chantal, not patented. In side-by-side comparisons conducted in El Quinche, Pichincha, Ecuador plants of the new *Aster* differed from plants of the cultivar Chantal in the following characteristics:

1. Plants of the new *Aster* were shorter yet broader than plants of the cultivar Chantal.
2. Plants of the new *Aster* had longer leaves than plants of the cultivar Chantal.
3. Plants of the new *Aster* had larger and taller inflorescences than plants of the cultivar Chantal.
4. Inflorescences of plants of the new *Aster* had more ray florets than inflorescences of plants of the cultivar Chantal.
5. Ray florets of plants of the new *Aster* were darker in color than ray florets of plants of the cultivar Chantal.
6. Plants of the new *Aster* had longer peduncles than plants of the cultivar Chantal.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster.*

The photograph at the top of the first sheet comprises a side perspective view of a typical fliowering stem of 'Esmguyama'.

The photograph on the second sheet is a close-up view of a typical inflorescence of 'Esmguyana'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the summer in El Quinche, Pichincha, Ecuador, in an outdoor nursery and under conditions which approximate those generally used in commercial cut flower *Aster* production. During the production of these plants, day temperatures ranged from 12 to 30° C. and night temperatures ranged from 5 to 12° C. Plants were about four to six months from planting rooted young plants when the photographs and the botanical description were taken.

Botancial classification: *Aster hybrida* cultivar Esmguyana.

Parentage:

*Female, or seed, parent.*—Proprietary *Aster hybrida* selection identified as Line 11, not patented.

*Male, or pollen, parent.*—Unknown *Aster hybrida* selection, not patented.

Propagation:

*Type.*—Terminal vegetative cuttings.

*Time to initiate roots.*—About 12 to 16 days at 17 to 25° C.

*Time to produce a rooted young plant.*—About 21 to 25 days at 17 to 25° C.

*Root description.*—Fine, fibrous; 162C in color.

*Rooting habit.*—Freely branching.

Plant description:

*Appearance.*—Herbaceous daisy-type cut flower *Aster*. Flowering stems upright and strong. Vigorous. Symmetrical branching habit with long lateral branches.

*Plant height.*—About 116 cm.

*Plant width.*—About 37 cm.

*Lateral branches.*—Quantity per plant: About 19. Length: About 55 cm. Diameter: About 4.4 mm. Internode length: About 3.3 cm. Strength: Strong. Texture: Smooth, pubescent; waxy. Color: 144A to N79B.

*Foliage description.*—Arrangement: Alternate, simple; sessile. Length: About 15 cm. Width: About 1.7 cm. Shape: Lanceolate. Apex: Acute. Base: Sheathed; lobes, slightly cordate. Margin: Minutely dentate. Texture, upper and lower surfaces: Glabrous, smooth; waxy. Color: Developing foliage, upper surface: 147A to 137A. Developing foliage, lower surface: 137A. Fully expanded foliage, upper surface: 139A to 147A. Fully expanded foliage, lower surface: 137B. Venation, upper surface: 144B. Venation, lower surface: 148D.

Inflorescence description:

*Appearance.*—Daisy-type inflorescence form with narrowly elliptic-shaped ray florets. Inflorescences terminal or axillary. Disc and ray florets develop acropetally on a capitulum. Inflorescences not fragrant. Inflorescences persistent. Inflorescences face mostly upright. Uniform and freely flowering habit.

*Flowering response.*—Plants flower year-round in Ecuador. Plants begin flowering about 15 to 16 weeks after planting.

*Postproduction longevity.*—Inflorescences maintain good color and substance for about two weeks as a cut flower and about 25 days on the plant.

*Quantity of inflorescences.*—About 34 inflorescences develop per lateral branch.

*Inflorescence bud.*—Height: About 8.6 mm. Diameter: About 7.4 mm. Shape: Nearly globose. Color: 137A to 138B.

*Inflorescence size.*—Diameter: About 3.8 cm. Depth (height): About 1.6 cm. Diameter of disc: About 1.4 cm. Receptacle diameter: About 1.2 cm. Receptacle height: About 9 mm.

*Ray florets.*—Number of ray florets per inflorescence/arrangement: About 59 in arranged in about two or three whorls. Length: About 2 cm. Width: About 4 mm. Shape: Narrowly elliptic. Apex: Obtuse with emarginations. Base: Attenuate. Margin: Entire. Texture, upper and lower surfaces: Smooth, glabrous. Orientation: Initially upright, then horizontal to recurved. Aspect: Mostly straight. Color: When opening, upper surface: N81A to 83B. When opening, lower surface: 83C to 86B. Fully opened, upper surface: 86A to N81A; color becoming closer to 90C to 86C with development. Fully opened, lower surface: 86B to 90C.

*Disc florets.*—Arrangement: Massed at center of receptacle. Number of disc florets per inflorescence: About 62. Length: About 9 mm. Diameter, apex: About 2.6 mm. Diameter, base: About 0.9 mm. Shape: Tubular, salverform, elongated. Apex: Five lobes; lobes acute. Color, immature: 153A. Color, mature: Apex: 11C. Mid-section and base: 145D.

*Phyllaries.*—Quantity per inflorescence: About 63. Length: About 6 mm. Width: About 1.2 mm. Shape: Narrowly triangular. Apex: Acute. Base: Truncate. Texture, upper and lower surfaces: Smooth, glabrous. Color, upper surface: 137A. Color, lower surface: 137B to 145C.

*Peduncles.*—Length, terminal peduncle: About 1.6 cm. Length, fourth peduncle: About 2.4 cm. Length, seventh peduncle: About 3.3 cm. Diameter: About 1.5 mm. Aspect: Erect to about 24° from vertical. Strength: Strong. Texture: Pubescent. Color: 146A.

*Reproductive organs.*—Androecium: Present on disc florets only. Quantity of stamens per disc floret: Four. Anther shape: Linear. Anther length: About 1.8 mm. Anther color: 7A. Pollen amount: Scarce. Pollen color: 7A. Gynoecium: Present on both ray and disc florets. Quantity per floret: One. Pistil length: About 1.3 cm. Stigma shape: Bilobed; lobes linear. Stigma color: 2D to 154D. Style length: About 8.3 mm. Style color: 145C. Ovary color: 157D to 155C.

*Seed.*—Length: With pappus, about 5 mm; without pappus, about 3 mm. Diameter: About 1 mm. Color: Dried, 199A.

Disease/pest resistnace: Resistance to pathogens and pests common to *Asters* has not been observed on plants grown under commercial greenhouse conditions.

Temperature tolerance: Plants of the new *Aster* have been observed to tolerate temperatures from about 7 to about 30° C.

It is claimed:

1. A new and distinct cultivar of cut flower *Aster* plant named 'Esmguyana', as illustrated and described.

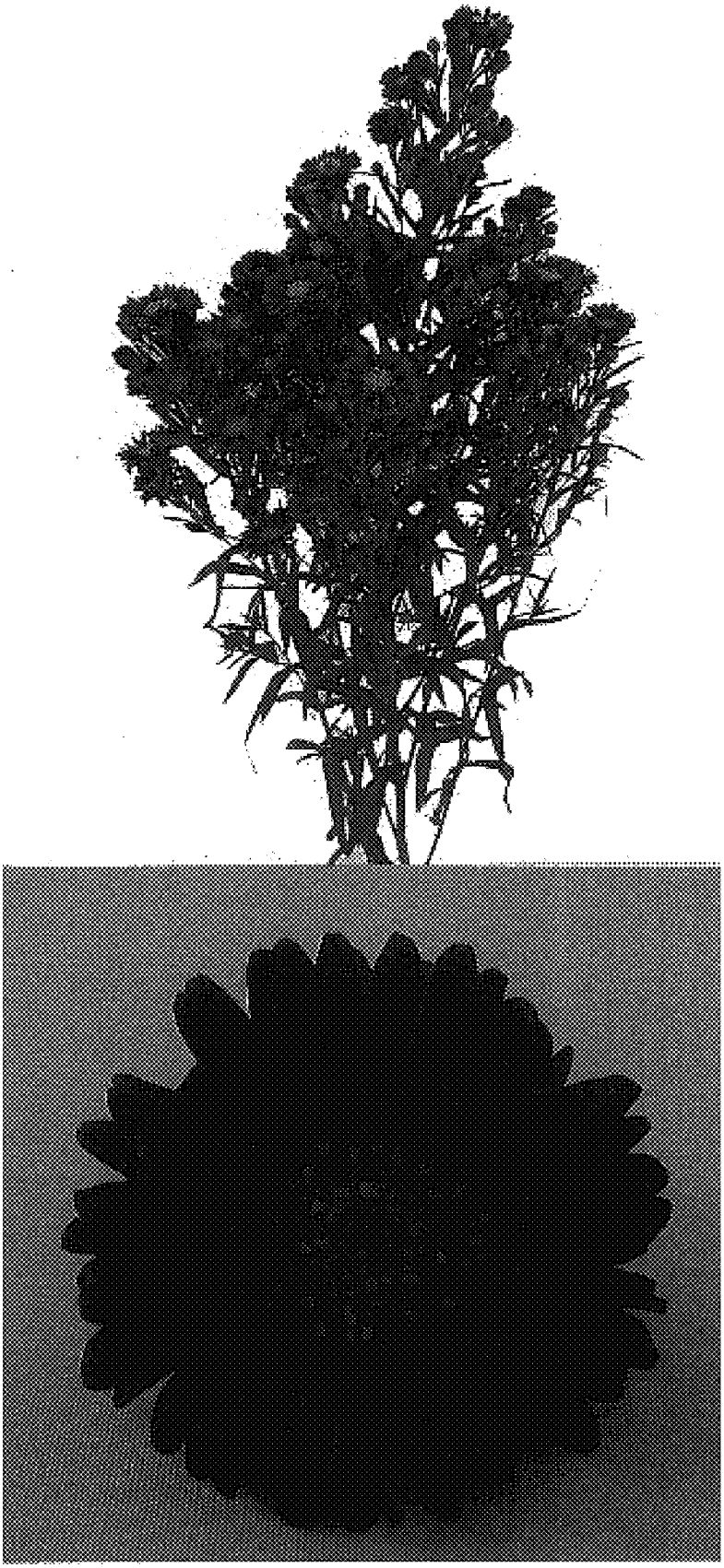

* * * * *